(12) United States Patent
Bake et al.

(10) Patent No.: US 10,327,785 B2
(45) Date of Patent: Jun. 25, 2019

(54) SURGICAL KIT FOR REPAIR OF ARTICULAR SURFACES IN THE TALOCRURAL JOINT INCLUDING SURGICAL SAW GUIDE

(71) Applicant: EPISURF IP-MANAGEMENT AB, Stockholm (SE)

(72) Inventors: Nina Bake, Lidingö (SE); Richard Lilliestråle, Stockholm (SE); Leif Ryd, Malmö (SE); Katarina Flodström, Danderyd (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 0 days.

(21) Appl. No.: 15/526,539

(22) PCT Filed: Nov. 13, 2014

(86) PCT No.: PCT/EP2014/074533
§ 371 (c)(1),
(2) Date: May 12, 2017

(87) PCT Pub. No.: WO2016/074733
PCT Pub. Date: May 19, 2016

(65) Prior Publication Data
US 2017/0325826 A1    Nov. 16, 2017

(51) Int. Cl.
*A61B 17/15*  (2006.01)
*A61B 17/17*  (2006.01)
(Continued)

(52) U.S. Cl.
CPC ............ *A61B 17/151* (2013.01); *A61B 17/15* (2013.01); *A61B 17/1775* (2016.11);
(Continued)

(58) Field of Classification Search
CPC .......... A61F 2/42; A61F 2/4202; A61B 17/15; A61B 17/151; A61B 17/17; A61B 17/1775
See application file for complete search history.

(56) References Cited

U.S. PATENT DOCUMENTS 6,673,116 B2 * 1/2004 Reiley .................... A61B 17/15
606/87
2008/0097617 A1 4/2008 Fellinger et al.
(Continued)

FOREIGN PATENT DOCUMENTS

WO    WO-2014/020562 A1    2/2014
WO    WO-2017/070318 A1    4/2017

OTHER PUBLICATIONS

Office Communication issued in international application No. PCT/EP2018/050889, dated Oct. 16, 2018.

*Primary Examiner* — Christopher J Beccia
(74) *Attorney, Agent, or Firm* — Drinker Biddle & Reath LLP (57) ABSTRACT

A surgical kit suitable for repair of articular surfaces in the talocrural joint, includes: a surgical implant having a cap with an outer surface conforming to a talus dome surface and an inner surface having a central implant anchoring peg extending perpendicularly from said inner surface, a hollow tubular shell suitable for correct pre-drilling for implantation of the surgical joint implant in the dome of the talus, and a saw guide conforming and fixable to the lower portion of the tibia and providing saw guide surfaces in at least one plane, suitable for osteotomy of a lower portion of a tibia to expose the dome of the talus.

9 Claims, 12 Drawing Sheets

(51) Int. Cl.
A61F 2/42 (2006.01)
A61F 2/30 (2006.01)

(52) U.S. Cl.
CPC ........ A61F 2/30942 (2013.01); A61F 2/4202 (2013.01); *A61F 2002/30299* (2013.01); *A61F 2002/30878* (2013.01); *A61F 2002/4207* (2013.01)

(56) References Cited

U.S. PATENT DOCUMENTS

| | | | | |
|---|---|---|---|---|
| 2010/0087824 | A1 | 4/2010 | Collazo | |
| 2010/0262150 | A1* | 10/2010 | Lian | A61B 17/15 606/87 |
| 2012/0239045 | A1* | 9/2012 | Li | A61B 17/15 606/88 |

* cited by examiner

FIG. 8A

SURGICAL KIT FOR REPAIR OF ARTICULAR SURFACES IN THE TALOCRURAL JOINT INCLUDING SURGICAL SAW GUIDE

TECHNICAL FIELD

The present invention relates in general to the surgical repair of osteochondral defects typically in the dome of the talus using surface implants

BACKGROUND

Introduction

Osteochondral defects of the talar dome are mostly caused by a traumatic event. They may lead to deep ankle pain on weight bearing, prolonged swelling, diminished range of motion, and synovitis. The mean cartilage thickness of the talar dome is in the range 1.2 to 1.4 mm. Cartilage defects are strongly linked to the subchondral bone. The main target in the treatment of talar osseochondral defects (OCDs) is repair of the subchondral bone. A healthy restored subchondral bone plate would decrease the pain, improve the load-bearing capacity of the ankle, and improve chondrocyte survival in the remaining cartilage Treatments Treatment options for OCDs are numerous. The highest success rates were reported for bone marrow stimulation, such as drilling or microfracturing, (85%) and osteochondral autograft transfer (87%). Because osteochondral autograft transfer can cause knee morbidity, the conclusion was that debridement and bone marrow stimulation remains the treatment of choice for primary OCDs (i.e., those without previous surgery) up to 15 mm.

During debridement and bone marrow stimulation, the OCD is preferably approached by anterior ankle arthroscopy with the ankle in full plantar flexion for adequate exposure of the defect.

However, the ankle is a congruent joint with limited surgical access. Some defects are located so far posteriorly that they may not be accessible by anterior ankle arthroscopy.

Lesions after failed previous surgery or large lesions can be treated by various alternative surgical methods, including autologous cancellous bone grafting, osteochondral autograft transfer, and autologous chondrocyte implantation (ACI). Although successful results can be achieved, disadvantages of these secondary methods include pain at the donor site, limited availability of graft material, and two surgical procedures in the case of ACI. An alternative without these disadvantages would be desirable. The methods mentioned above are sometimes combined with osteotomy for better access to the talar dome.

Metal Implants

Because of the disadvantages of current secondary treatment methods, metal resurfacing inlay implants have been developed and started to reach the market. A precise surgical technique is required in terms of implantation depth, position, and orientation because of the biomechanical properties of the ankle joint. A protruding implant may damage the opposite cartilage by causing excessive contact pressures during loading, which is thought to be due to "plowing" of the cartilage. On the other hand, a deep implant might result in collapse of the adjacent cartilage due to insufficient support.

If the lesion is located on the medial side of the talar dome (ca 60% of cases), most of these treatment options require a medial malleolar osteotomy in order to obtain access to the talar dome. A medial malleolar osteotomy is an established approach for the operative treatment of medial osteochondral defects of the talar dome and fractures of the talar body. There are different varieties of osteotomy to get access to the talar dome. A commonly used osteotomy is the oblique medial malleolar osteotomy, which is a crucial step in the surgical implantation of the resurfacing inlay implants. To obtain a congruent joint surface after refixation, the osteotomy should be directed perpendicularly to the articular surface of the tibia at the intersection between the tibial plafond and medial malleolus. At an instructional course on the metallic implantation technique, surgeons experienced technical difficulties performing a successful medial malleolar osteotomy. The difficulties included sawing at an angle that allowed refixation of the distal fragment without creating an articular incongruence, as well as identifying the intersection between the tibial plafond and medial malleolus. Thus, knowledge of the angle of the osteotomy relative to an anatomic landmark such as the long tibial axis would be helpful for use during surgery, as well as surgical tricks to identify the intersection.

It has been reported that a medial malleolar osteotomy frequently led to local osteoarthritis and less favorable clinical findings than arthrotomy without osteotomy.

The advantages of implants over complete replacement of the joint have stimulated a further development of smaller implants that can be implanted with less invasive surgery. In this development there has also been an effort to achieve small joint implants, suitable for repair of a small bone and/or cartilage injury that have a minimal influence on the surrounding parts of the joint. In the current development, such small implants are designed with an implant body that may be formed as a mushroom cap with a hard surface to face the articulating side of the joint and a bone contacting surface engaging the bone below the damaged part of cartilage. The shape and the curvature of the articulating surface of the implant may be designed to be a reconstitution of the shape and the curvature of the part of the joint when it was undamaged. Such implants are usually designed as mushrooms with an implant body or head and with a peg or a rod projecting from the bone contacting side of the implant body for anchoring the implant into the bone. The cap of the mushroom for repair of the talus dome is often slanted or irregular to conform to the shape of the original undamaged ridge or dome of the talus.

There is a lack of talar metal resurfacing implants with an exact match of the undamaged talar anatomy, as well as metal resurfacing implants that can be placed not only at the edge of the medial talar dome, but placed more centrally on the medial talar dome.

OBJECT OF THE INVENTION

Implants having a top cap surface customized to each patient to replicate the surface of the talus dome before it was injured, must be implanted so that the forces, applied during standing and walking via the lower condylar surfaces of the tibia against the new implant will act axially in relation to the implantation peg, for optimum force absorption and length of life. The anatomy of the talocrural area differs from that of the knee in that it is very difficult for the surgeon to access the dome of the talus. It is covered by the lower condylar surface of the tibia, as well as being encased by a many different muscles, tendons and ligaments extending between the tibia and the calcaneus, the navicular and the talus, particular the medial (deltoid) ligaments and flexor digitorum longus and the tibialis posterior muscles. Any severing of these muscles and tendons to gain access to the talus dome will create exceptional and sometimes permanent problems as regards repair and rehabilitation.

Furthermore, if a corner block of the lower tibia is sawn out in order to gain access to the talus dome, for correct healing of the tibia when the block is replaced, it is necessary that the bone be sawn quite precisely on the first try, so that the bone segment will fit precisely in place when put back and screwed in place.

It is thus necessary to expose the talus dome by cutting out a corner of the lower medial tibia, under a number of difficult constrictions:
avoiding all important tendons, muscles and ligaments and leaving them attached and intact,
avoiding the anterior tibial artery,
providing enough exposed space to correctly drill for and drive in the implant at the correct angle,
making the bone cuts precise and correct on the first try,
facilitating replacement and fixation of the corner block of the tibia in its correct position for healing.

A kit according to the invention makes this possible in a precise and reproducible manner, providing for an operation which would be almost impossible to achieve with free-hand cutting, and placement of the implant.

SUMMARY

Thus the entire complex of problems listed above finds its solution in the invention as defined in the appended main patent claim.

BRIEF DESCRIPTION OF DRAWINGS

Embodiments of the invention will now be described in more detail with reference to the appended drawings, wherein.

DETAILED DESCRIPTION

Figure 1:
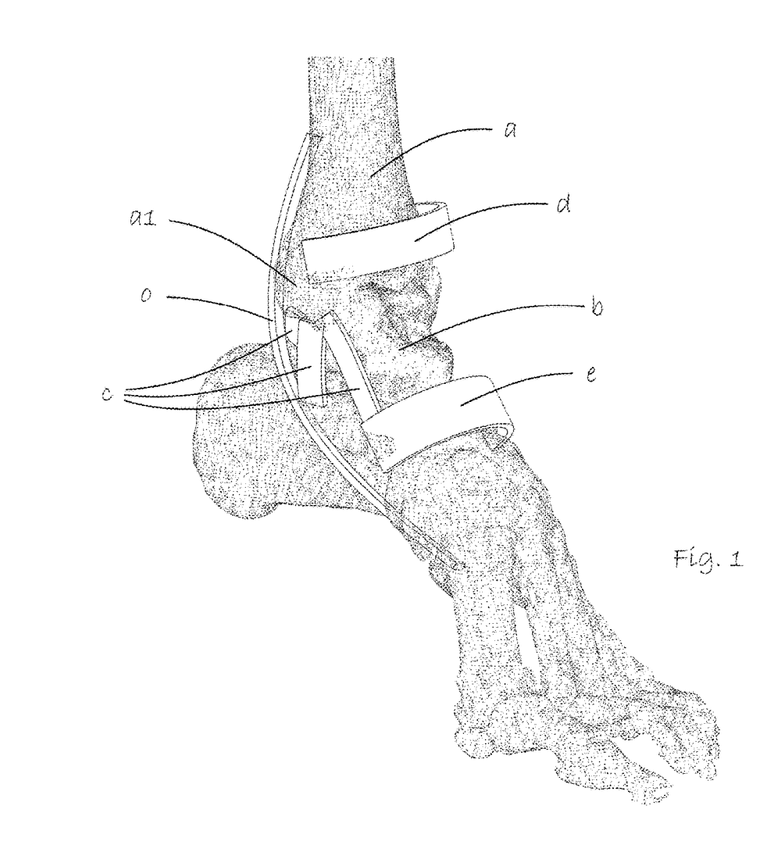
FIG. 1 shows a skeletal view of the foot with ligaments, to illustrate the area of use of the invention.

FIG. 1 shows, to show the area of use of the present invention, the skeletal foot of a patient to receive a customized surgical implant to repair the condylar dome surface of the talus. The bones and ligaments of the area of the foot where the kit according to the invention is to be used constitute, of course, no part of the present invention and are therefore labelled with letters. The lower medial end of the tibia a is shown as well as the talus b and, schematically, the medial deltoid ligaments c covering this joint and attached to the malleolus a1.

o indicates purely schematically the tendons of the flexor digitorum longus and the flexor hallucis longus. d indicates the superior extensor retinaculum.

Figure 2:
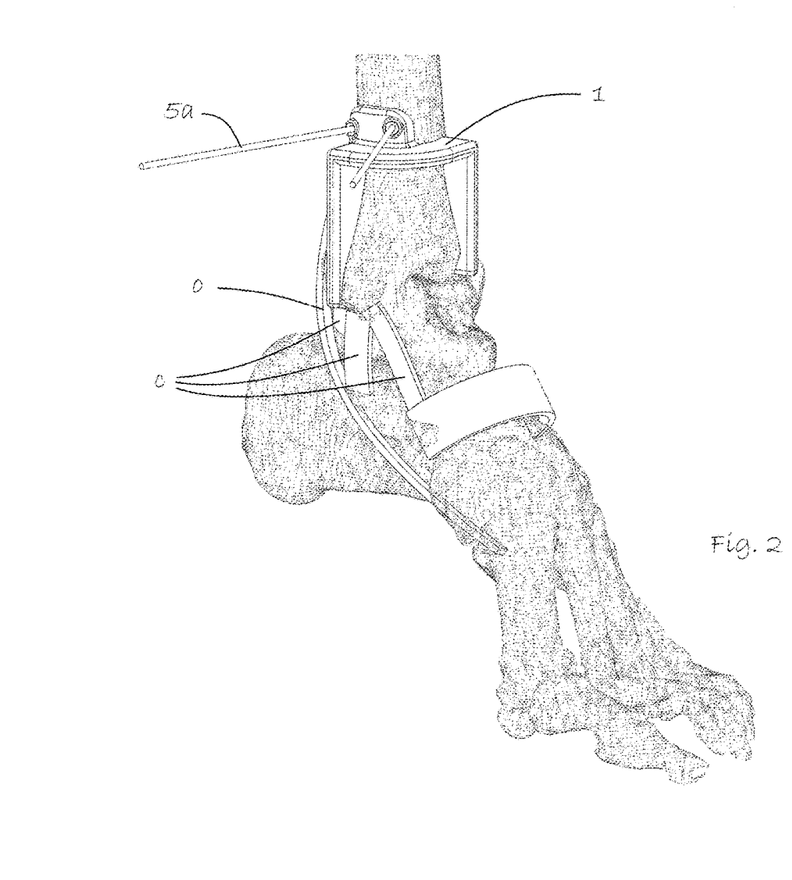
FIG. 2 shows the same skeletal view as FIG. 1 with a saw guide mounted in place.

FIG. 2, shows the same view as FIG. 1 but with a saw guide 1 in a surgical kit according to the invention mounted in place on the distal end of the tibia a using pins 5a. The superior extensor retinaculum d shown in FIG. 1 is not shown in this figure. It has been pulled down out of the way of the saw guide using a surgical hook, without any need to cut into this retinaculum.

Figure 3:
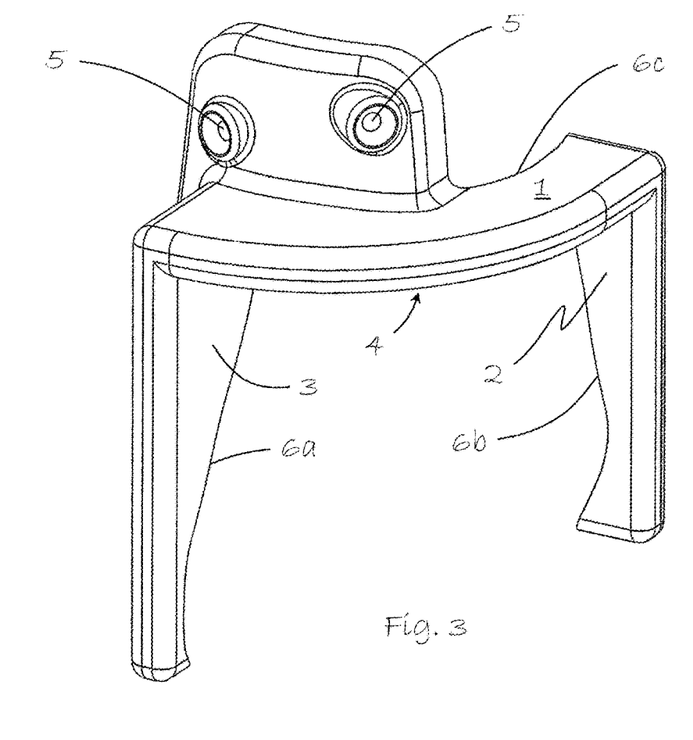
FIG. 3 shows the saw guide of the invention and which is included in the kit according to the invention.

FIG. 3 shows alone the saw guide 1 of the kit according to the invention. Each saw guide is customized via imagery of the patient's tibia through e.g. MRI, CT or X-ray. Each saw guide has surfaces 6a-c conforming to the particular patient's tibia. One of the surfaces 6a is longer to cover the malleolus. In this particular non-limiting embodiment of the invention, the saw guide 1 provides three saw guide surfaces 2, 3, 4, respectively, in the sagittal, coronal and transverse planes respectively. Two pin holes 5 are provided for securing the saw guide in place on the tibia.

Figure 4:
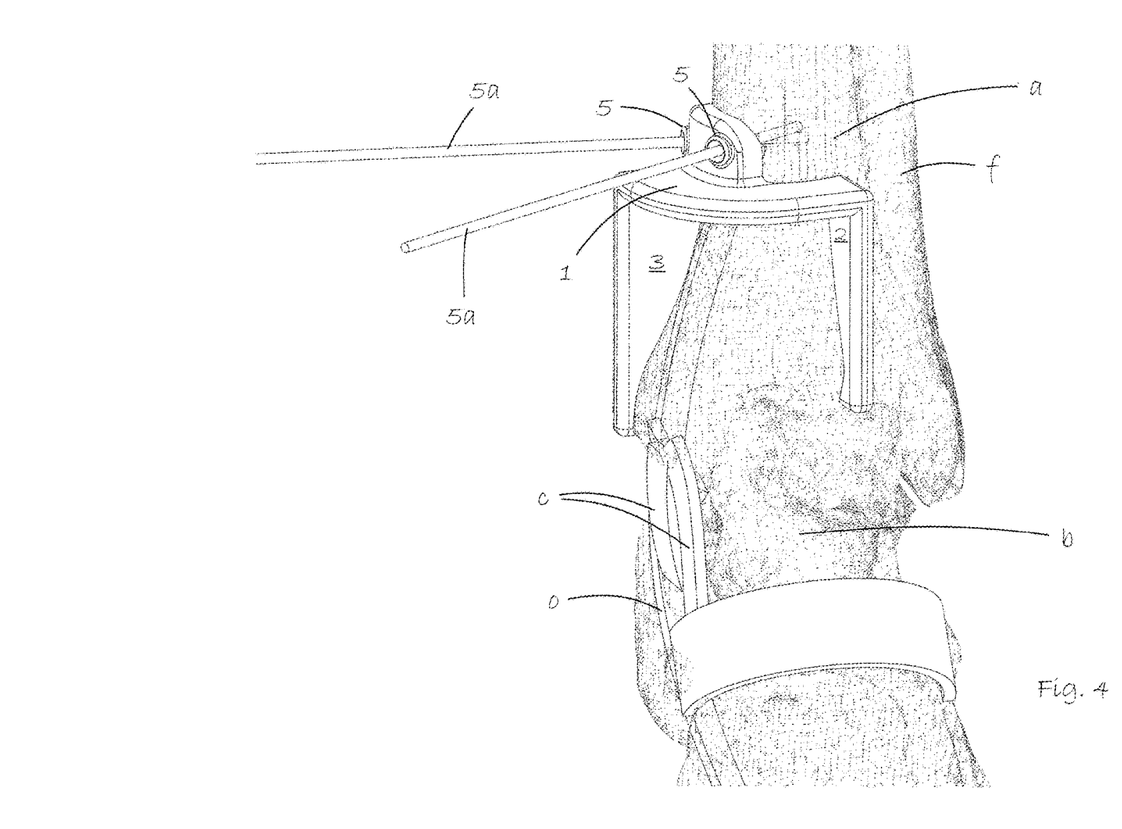
FIG. 4 shows different views of the saw guide according to the invention mounted in place on the distal medial end of the left tibia.

The saw guide is individually made specific to the patient's specific anatomy and to the specific damage to the talus, possibly through the following saw guide design steps:
a. identifying a subchondral damage of the talus dome through radiological images such as MR, CT or X-ray images or through arthroscopy.
b. planning the size and the location of an osteotomy needed to get access to the talar dome in order to treat the subchondral damage
c. creating a 3D model of the tibial bone from radiological images such as MR, CT or X-ray images
d. virtually designing a patient specific osteotomy guide based on the 3D model of the tibial bone and the size and location of the osteotomy needed FIG. 4 is a close-up view of the saw guide put in place on the lower end of the tibia in an initial stage of the procedure utilizing the kit according to the invention. The skin has first been pulled away exposing the anterior medial area of the tibia where the patient customized saw guide is to be mounted. Pins 5a are driven into the bone through the pin holes 5 at different angles to fix the saw guide securely in place.

Figure 5:
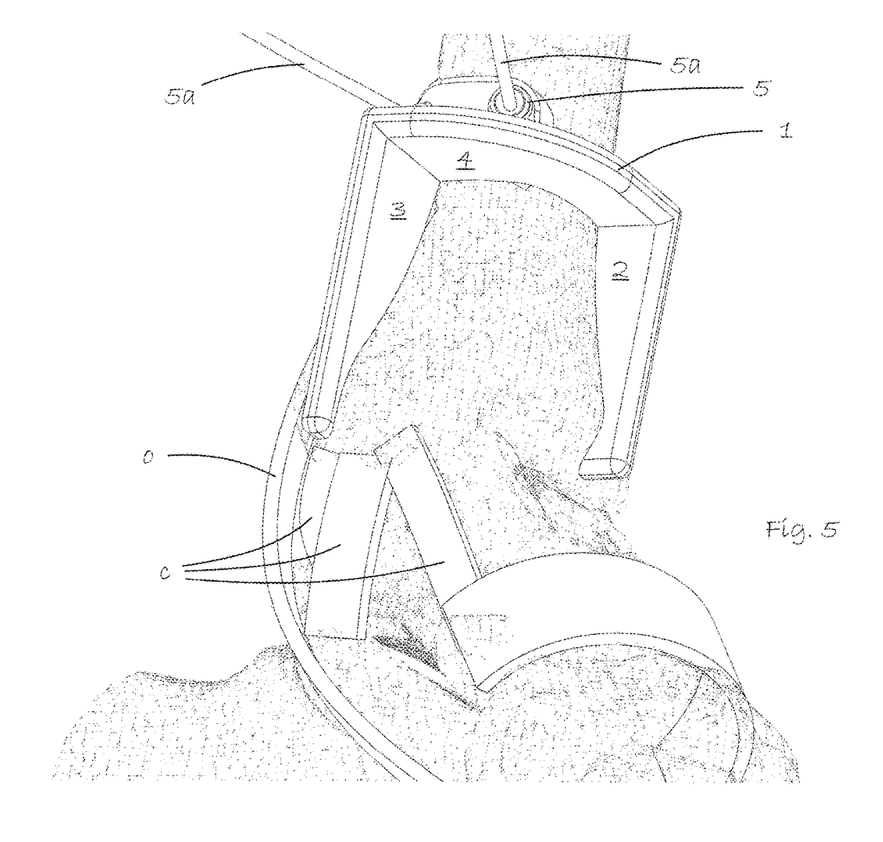
FIG. 5 shows a view from another angle with the saw guide 1 mounted in place and more clearly showing the three guide surfaces 2, 3, 4 used for precision cutting a quadrant section of the tibia.

FIG. 5 shows a view from another angle with the saw guide 1 mounted in place and more clearly showing the three guide surfaces 2, 3, 4 used for precision cutting a quadrant section of the tibia to expose the dome of the talus.

Figure 6:
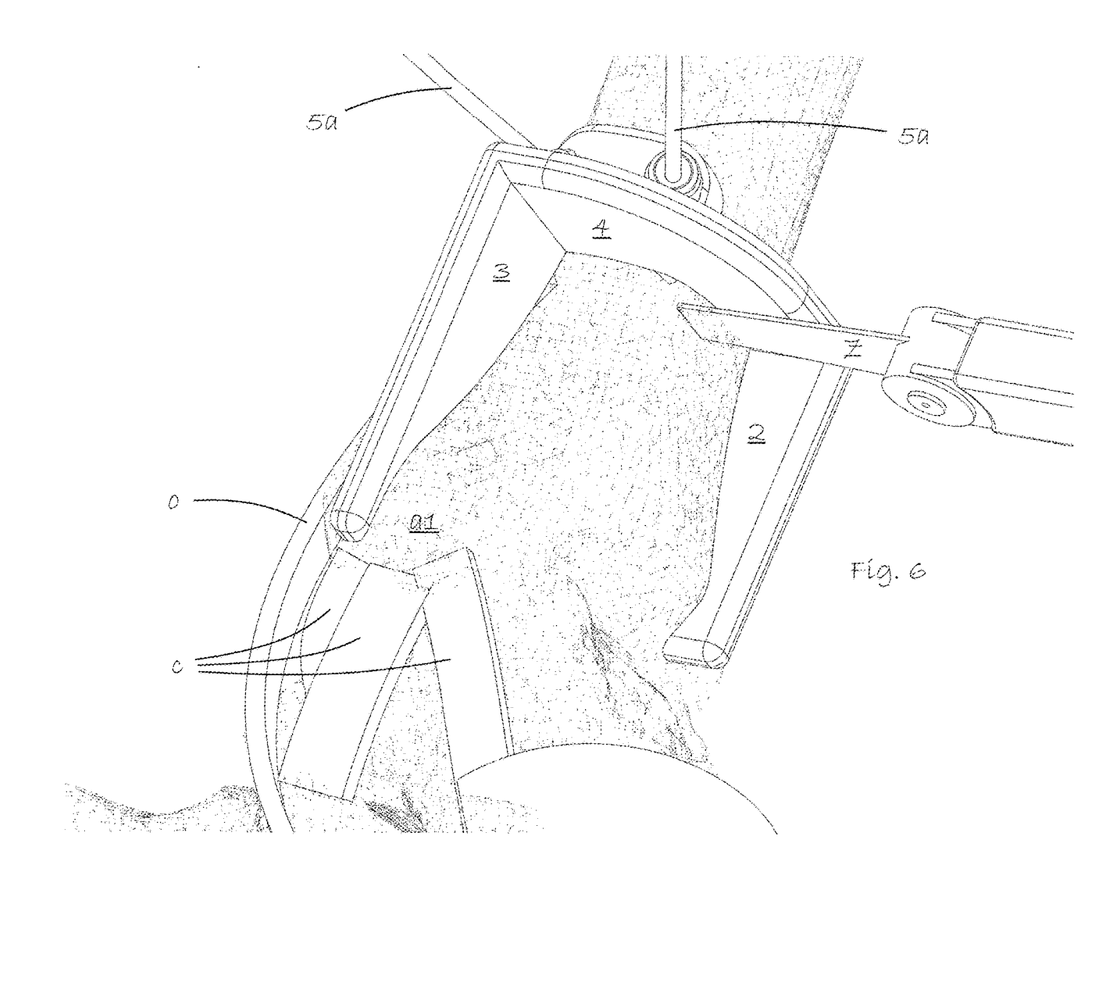
FIG. 6 shows the saw guide in use in making a transverse cut with surgical saw.

FIG. 6 shows use of a surgical saw 7 to make a transverse cut along the guide surface 4 using inserted pins 5a to prevent the cut from penetrating deeper than intended. A form-fitting thin talus guide (not shown) is slipped in between the tibia and the talus to protect the talus as cuts are made along the guide surfaces 2 and 3. The quadrant section of the tibia is finally removed by a flat surgical chisel cutting any remaining bone material in the inner corner.

Figure 7:
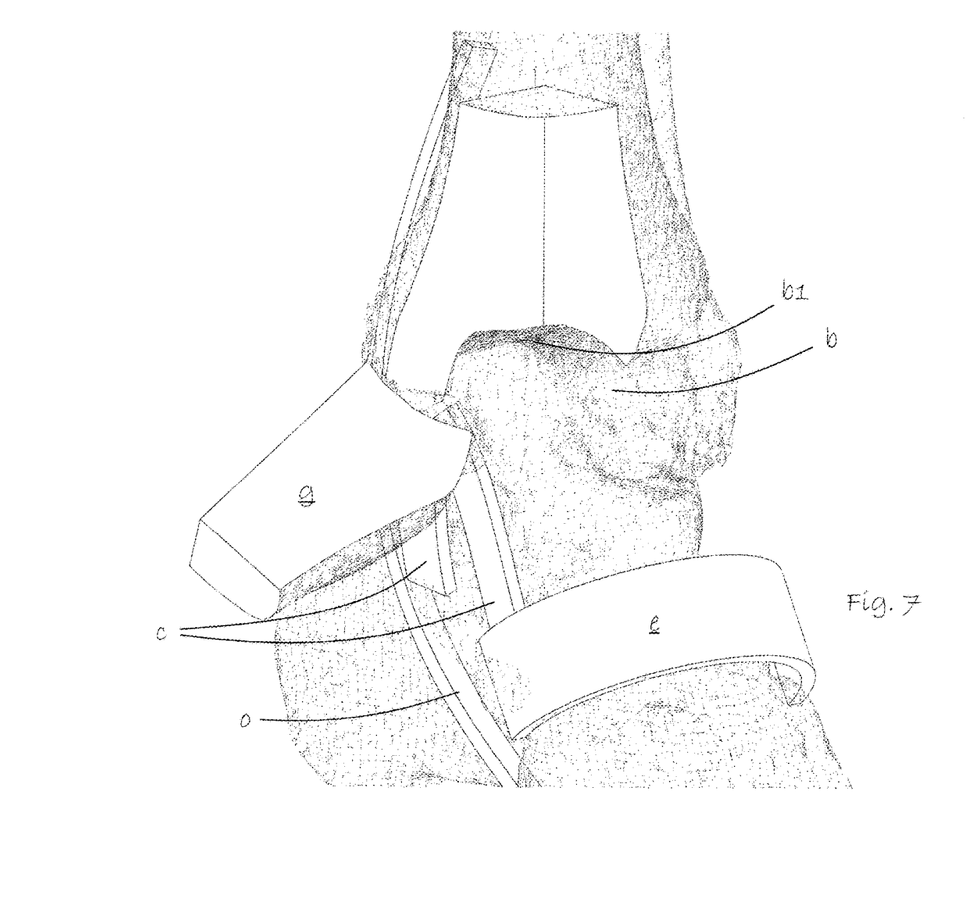
FIG. 7 shows a view of the talocrural area with the sawn out corner block of the tibia folded out to expose the talus dome.

Referring now to FIG. 7, the sawn out bone quadrant of the tibia is then folded forwardly and outwardly taking care not to damage the medial deltoid ligaments c continually attached between the bone quadrant of the tibia and the talus b. The talus dome is thus exposed. The dome area to be repaired with the implant is labelled b1.

Figure 8A:
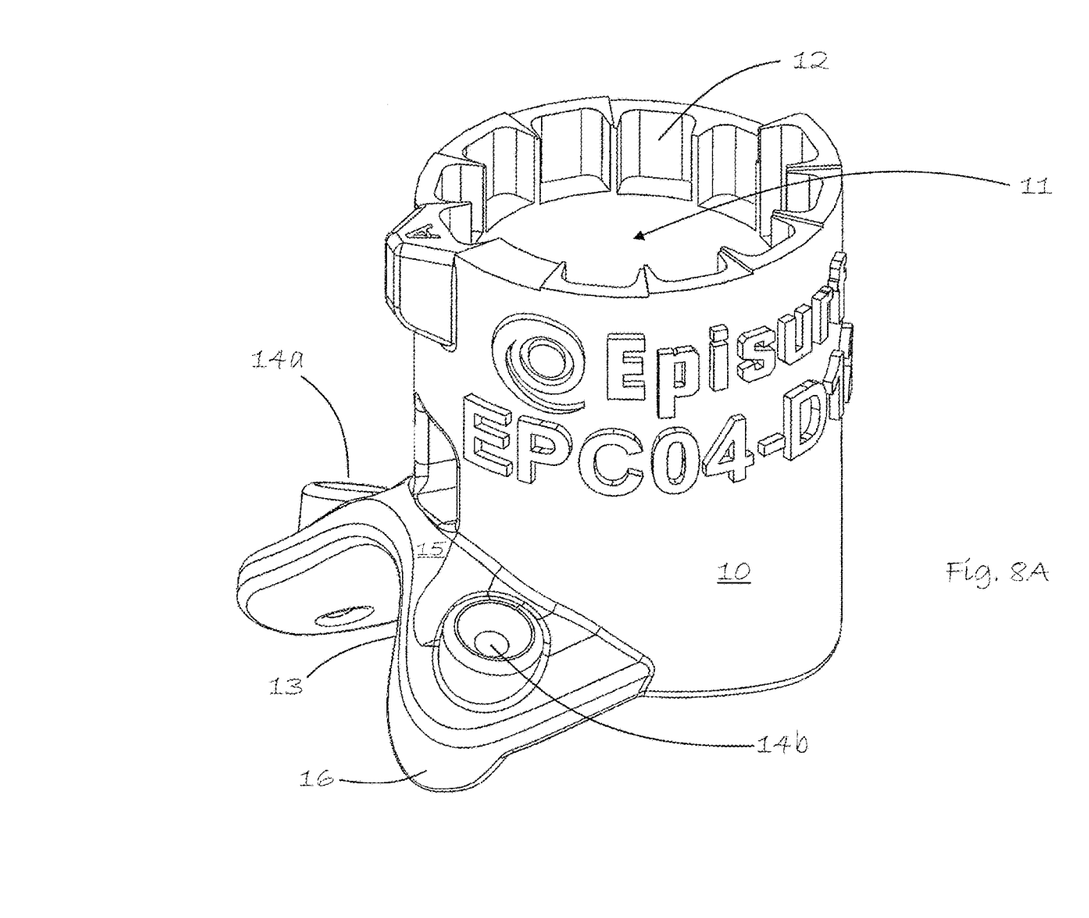
FIGS. 8A and 8B show the hollow drill guide included in the surgical kit according to the invention
Figure 8B:
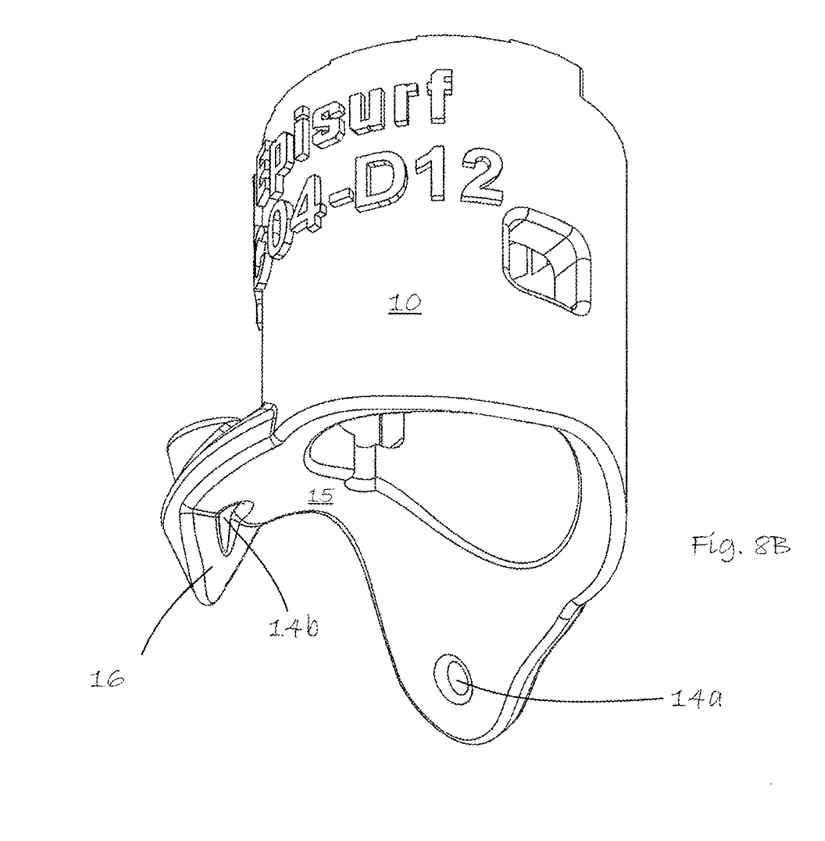

FIGS. 8A and 8B show alone one exemplary drill guide 10 in the kit according to the invention. A drill sleeve (not shown) is inserted into the hollow center of the drill guide, fitting into the height adjustment sprockets 12 at the top of the interior 11 of the drill guide. The lower surfaces of the drill guide conform to the condylar surfaces of the talus which are to be provided with a replacement implant. A saddle shaped flange 15 conforming to the ridge of the talus dome of the particular patient extends from the drill guide cylinder. The flange has medial and lateral pin holes, 14a and 14b respectively, for securely mounting the drill guide in place on the talus dome. It is also possible, in a non-limiting embodiment, to provide the saddle shaped flange 15 with a downwardly bent corner portion or hook 16, disposed at the lateral pin hole 14b. This corner hook portion 16, which is most visible in FIG. 8B, is designed to help in correctly positioning and anchoring the drill guide on the neck of the talus b. The entire drill guide and in particular the surface of the saddle shaped flange 15 is individually dimensioned to the patient's talus. The saw guide 1 is dimensioned to provide, with only three saw cuts a tibia quadrant piece which when folded out provides enough space for the drill guide 10 and for vertical downward drilling so that the peg will be mounted coaxial or close to coaxial to the downward forces exerted, when walking, by the end of the tibia against the implant, with no lateral forces tending to dislodge the implant over time.

Figure 9:
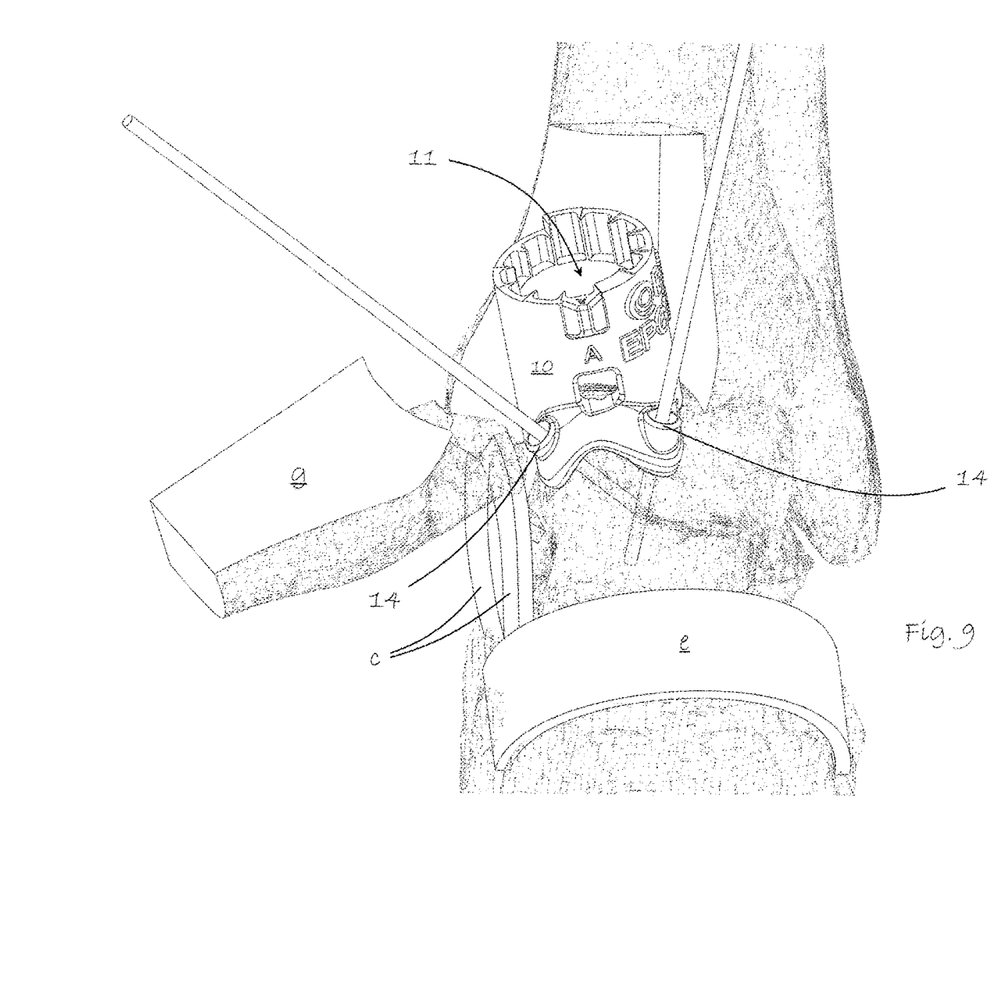
FIG. 9 shows the drill guide mounted in place on the talus dome.

FIG. 9 shows the drill guide fixed in place on the dome of the talus. Just a large enough quadrant section of the tibia has been sawn out to make room for the drill guide and the room needed to use the guide, now placed directly over the area of the talus to be repaired. The drill guide is also directed so as to provide the correct angle for the peg of the implant so that the angle of the peg ideally is aligned with the forces exerted by the tibia when walking.

Figure 10:
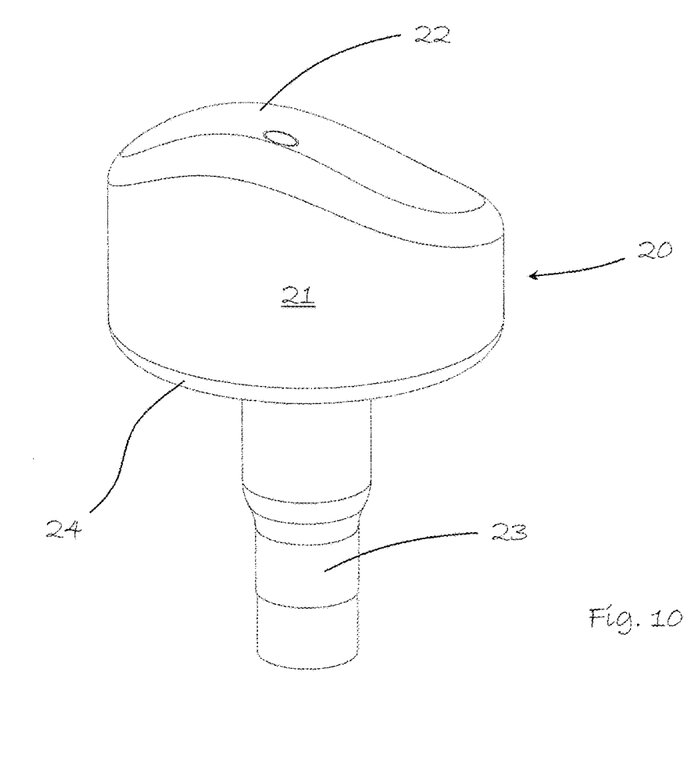
FIG. 10 shows a patient customized talus implant.

FIG. 10 shows in detail a patient customized implant 20 made in a biocompatible metal, metal alloy or ceramic. More specifically it may comprise any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia.

The implant has typically a cap diameter of 12 or 17 mm or even 20 mm, but may also assume other diameters within this range.

The implant has a cap 21 having a top surface 22, comprises a cobalt chrome alloy (CoCr) or stainless steel, diamond-like carbon or a ceramic and the top surface 22 has been custom surfaced to match the undamaged talus dome of the particular patient. The implant has a cap 21 with on its outside a new joint surface and on its inside, in this particular embodiment, a bone facing surface with a ridge 24 which lodges in a drilled groove as will be explained below.

Extending downwardly perpendicularly and centrally from the cap 21 is a mounting peg 23, for insertion into a hole drilled in the talus dome.

This individually shaped implant can be made on the basis of CT-scans, MR-imaging or X-ray images, by the method described in Application No. PCT/EP2014/064749.

Figure 11:
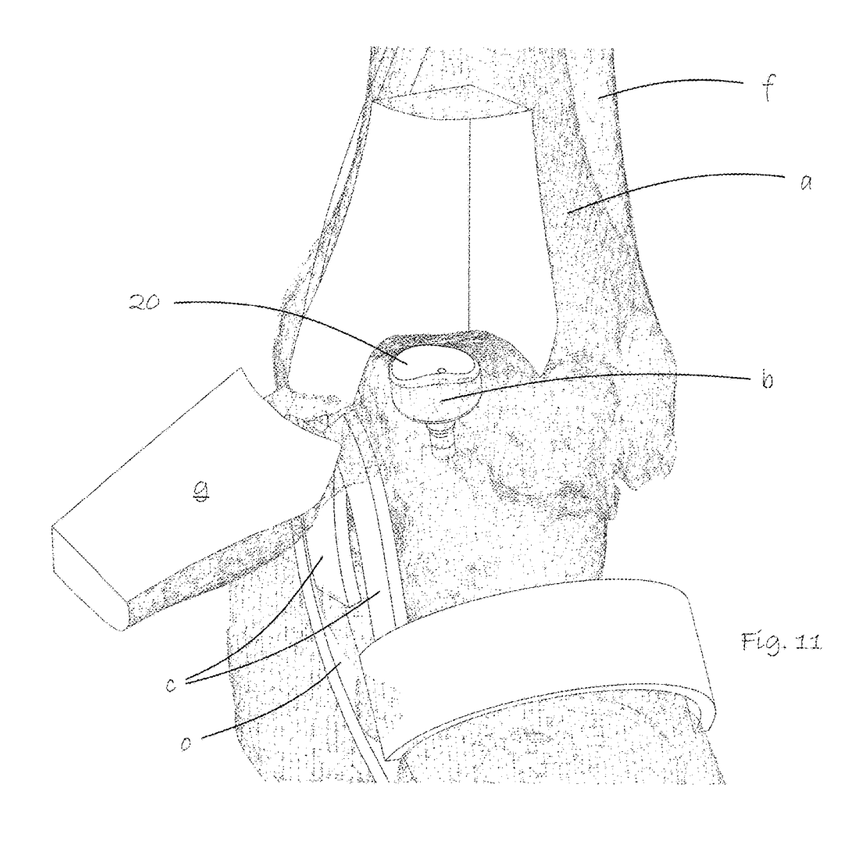
FIG. 11 shows the talus implant hammered into place in the talus dome, replacing the damaged surface of the talus joint.

FIG. 11 shows the implant 20 in its final placement after being hammered down into its hole, whereby the peripheral rim around the lower surface of the cap lodges in a groove in the hole in the talus. The cut out tibia bone quadrant piece g is still folded out. The quadrant piece g is then folded back into its original position and screwed into place preferably using two titanium screws into either vertical surface. According to a preferred operational method, the two screw holes are pre-drilled through the quadrant piece and into the tibia, before the saw cuts are made to make sure that the tibia quadrant piece will be remounted in exactly its original position.

One Exemplary Surgical Procedure for use of the Invention:

In the following one exemplary procedure is described for the use of the kit and the saw guide according to the invention. This description is of course not limiting of the invention. Rather other procedures may be used, for example with a block of the tibia removed with surfaces at other angles than the orthogonal angles described below. It is also possible that the patient customized saw guide only provide for a cut in one plane, e.g. for severing a portion of the malleolus, straight off, if, for example, only the medial portion of the talus dome need be exposed. The surgical saw guide can further be used for other treatments than in connection with the implant of the present invention. The saw guide can for example be used for access to the talus dome for osteochondral treatment through grafting or micro fracturing.

Procedure:

1. Incision: Wiberg surgical raspatory file. Hohmann retractors used to separate the skin after incision. White positioner.
2. A Hintermann distractor is used for separation.
    The patient customized saw guide is placed on the tibia after the bone has been exposed. Two 1.6 mm pins are inserted through pin holes in a form fitting flange on the saw guide and are driven into the tibia, holding the saw guide securely in place for all three orthogonal saw cuts to follow.
3. Two bore holes of 3.5-4 mm are first drilled through the intended osteotomic tibial quandrant and past the sagittal and coronal guide planes into the bone therebehind. These holes are drilled at this time to assure exact replacement and fixation of the removed bone quadrant in its exact original position.
4. First the saw cuts in the transverse plane and in the coronal plane are made up to stop pins driven in to prevent cutting into the tibia beyond the quadrant block form to be removed.
5. A form fitting talus protector shield is slipped in anteriorly from between the talus dome and the malleolus and the lower condylar surface of the tibia, while avoiding the medial ligaments and the flexor digitorum longus and the tibialis posterior muscles. It is now possible to make the final cut in the sagittal plane without damaging the talus surface.
6. A flat and broad surgical chisel is used to remove any remaining bone holding the quadrant to the rest of the tibia.
7. The saw guide is removed.
8. The bone quadrant is pulled out and folded forward and downward all the while preserving the vital attachment of the medial (deltoid) ligaments to the removed tibia quadrant and to the calcaneus and the navicular.
9. The patient customized form fitting drill guide (Epi-guide®) in the form of a tubular shell is mounted in place on the talus dome, covering with its hollow part the damaged area of the talus to be repaired. It extends with a saddle shaped mounting flange forward along the ridge of the talus. Pins through the mounting flange securely fix the drill guide to the talus.
10. The patient customized saw guide has assured that a bone quadrant has been sawn and removed in one try, which is large enough to provide access to the damaged area of the talus dome, to allow for vertical mounting and anchoring of the drill guide, to allow for vertical drilling into the talus through the drill guide, and to allow for hammering the implant into place in the drilled hole in the talus.
11. A drill sleeve is inserted into the drill guide. Cartilage is cut away and a double drill (12-17 mm/4 mm) is used to drill the deeper (4 mm diameter) hole for the peg and the shallow hole for the cap, which may have a slight peripheral rim on its underside.
12. A second drill sleeve (height adjustment sleeve) which is adjustable to the correct depth is inserted and fine-tuning of the drilling depth is performed.
13. A dummy implant (Epidummy®) with a handle and of slightly smaller diameter than the real implant (Episealer®) is inserted into the drilled double hole to check for correct depth and postion of the hole. The dummy is then pulled out.
14. The drill guide is then removed.
15. The patient customized implant (Episealer®) is then pushed into place and then tapped finally into place using a mandril. The tibias quadrant piece which has been folded out exposes enough space within the tibia and above the talus dome to enable drilling for and insertion of the implant peg in the proper direction so that downward forces exerted by the tibia, when walking for example will be exerted largely in the direction of the peg so that no lateral forces will be exerted tending to dislodge the implant over time.
16. The excised tibia quadrant is then folded up into its original position and two screws screw it precisely into its original position by virtue of the fact that the deep screw holes were drilled into the intact tibia before the sawing operation.
17. The Hohmann skin retractors are removed and the tissue is sutured together.

The surgical kit according to the invention makes it possible to perform the above described surgical implant procedure which will make it possible to:
avoid all important tendons, muscles and ligaments and leaving them attached and intact,
provide enough exposed space to correctly drill for and drive in the implant at the correct angle,
make the bone cuts precise and correct on the first try,
make possible precise reattachment of the tibia quadrant piece to its original position for healing and correct alignment of the joint.

Aspects of a surgical procedure in which the kit and the saw guide of the invention are used could be defined in the following definitional points ordered A, B and C:
A. Method of joint implant surgery for repair of articular surfaces in the talocrural joint, comprising:
a) Fixing a patient customized saw guide (1) conforming and fixable to the lower medial anterior portion of the tibia and providing saw guide surfaces (2,3,4) in three different planes, suitable for osteotomy of a lower medial anterior piece of a tibia to expose the dome of the talus,
b) Making cuts along each of said three saw guide surfaces excising a lower medial anterior quadrant of the tibia,
c) Folding said lower medial anterior quadrant piece forward and outward, preserving the attachment of medial deltoid ligaments and exposing the damaged condylar area of the talus dome,
d) Mounting a patient customized form fitting hollow drill guide comprising a tubular shell in place on the talus dome, covering with its hollow part the damaged area of the talus to be repaired,
e) Drilling in said drill guide with a double drill having a narrow diameter deeper drill and a larger diameter shallower drill providing a bore for a talus implant,
f) Removing said drill guide,
g) Inserting into said bore a surgical implant (20) having a cap (21) with an outer surface (22) conforming to a talus dome surface and an inner surface having a central implant anchoring peg (23) extending perpendicularly from said inner surface,
h) Replacing said excised lower medial anterior quadrant piece into its original position and fixing it in place.
B. Method according to Definition A, wherein, said saw guide surfaces define transverse, sagittal and coronal planes.
C. Method according to Definition B, prior to step b) i.e. making cuts along each of said three saw guide surfaces, also comprising drilling two screw holes perpendicular to the sagittal and coronal planes through the intended lower medial anterior quadrant piece, penetrating beyond the planes defined by the sagittal and coronal guide surfaces.

The invention claimed is:

1. A surgical kit suitable for use in osteotomy surgery for repair of articular surfaces in the talocrural joint, comprising:
a surgical implant with an outer surface conforming to a talus dome surface;
a hollow tubular shell suitable for correct pre-drilling for implantation of the surgical joint implant in the dome of the talus; and
a saw guide conforming and fixable to the lower portion of the tibia and providing a saw guide surface in one plane, suitable for osteotomy of a lower portion of a tibia to expose the dome of the talus, wherein the saw guide is adapted to conform to the lower medial anterior portion of the tibia and is configured to provide for a saw cut in one plane for severing a portion of the malleolus to gain access to the medial portion of the talus dome, and wherein the saw guide is configured to provide for said saw cut in one plane to temporarily expose the dome of the talus by the saw cutting out of a tibia piece in the temporary osteotomic removal of a distal portion of the tibia for implantation of the surgical implant in the dome of the talus.

2. The surgical kit according to claim 1, wherein said hollow tubular shell is customized to exactly fit the talus dome of a patient to be treated.

3. The surgical kit according to claim 1, wherein said saw guide is patient uniquely customized with surfaces and dimensions to exactly fit the lower medial anterior portion of the tibia of a specific patient to be treated.

4. The surgical kit according to claim 1, further comprising a talus protecting shield suitable for insertion between the talus dome and the malleolus and the lower condylar surface of the tibia.

5. The surgical kit according to claim 1, wherein said saw guide is suitable for osteomy of a lower portion of a tibia to expose the dome of the talus for implantation of the surgical implant in the dome of the talus and said surgical implant is customized to an undamaged talus dome of a specific patient to be treated.

6. The surgical kit according to claim 1, further comprising a talus protecting shield suitable for insertion between the talus dome and the malleolus and the lower condylar surface of the tibia.

7. The surgical kit according to claim 2, further comprising a talus protecting shield suitable for insertion between the talus dome and the malleolus and the lower condylar surface of the tibia.

8. The surgical kit according to claim 3, further comprising a talus protecting shield suitable for insertion between the talus dome and the malleolus and the lower condylar surface of the tibia.

9. The surgical kit according to claim 1, wherein the saw guide is configured to provide for a cut in one plane only for severing a portion of the malleolus for exposing the medial portion of the talus dome, thereby providing for the temporary osteotomic removal of a piece of the tibia with surfaces at other angles than the orthogonal angles to be removed, and wherein the design of said saw guide is individually patient customized on the basis of radiologically obtained patient data.

* * * * *